United States Patent [19]

Alliger

[11] E Patent Number: Re. 31,779

[45] Reissued Date of Patent: Dec. 25, 1984

[54] GERM-KILLING COMPOSITION AND METHOD

[75] Inventor: Howard Alliger, Melville, N.Y.

[73] Assignee: Alcide Corporation, Westport, Conn.

[21] Appl. No.: 140,444

[22] Filed: Apr. 17, 1980

Related U.S. Patent Documents

Reissue of:

[64] Patent No.: 4,084,747
Issued: Apr. 18, 1978
Appl. No.: 670,674
Filed: Mar. 26, 1976

[51] Int. Cl.[3] ..... A01N 3/00

[52] U.S. Cl. ..... 252/187.23; 424/149; 424/317; 422/20; 422/28

[58] Field of Search ..... 252/187 R, 188.3 R, 252/187.23, 187.21; 424/65, 317, 149; 239/4; 422/20, 28, 29

[56] References Cited

U.S. PATENT DOCUMENTS

| | | | |
|---|---|---|---|
| 2,071,091 | 2/1937 | Taylor | 167/17 |
| 2,988,514 | 6/1961 | Robson et al. | 252/187 R |
| 3,065,040 | 11/1962 | Walbet et al. | 8/108 |
| 3,124,506 | 3/1964 | Holman | 424/65 |
| 3,271,242 | 9/1966 | McNicholas et al. | 167/17 |
| 3,585,147 | 6/1971 | Gordon | 252/187 R |
| 3,843,548 | 10/1974 | James | 252/187 H |
| 3,912,450 | 10/1975 | Boucher | 21/54 A |
| 4,330,531 | 5/1982 | Alliger | 424/149 |

FOREIGN PATENT DOCUMENTS

| | | | |
|---|---|---|---|
| 959238 | 12/1974 | Canada | 252/187 A |

*Primary Examiner*—Josephine Barr
*Attorney, Agent, or Firm*—Hopgood, Calimafde, Kalil, Blaustein & Judlowe

[57] ABSTRACT

Germ-killing composition produced by contacting an acid material, preferably consisting of at least about 15% by weight of lactic acid, with sodium chlorite in aqueous media, the amount of acid being sufficient to lower the [PH] *pH* of the aqueous media to less than about 7. Methods of disinfecting and sanitizing include application of either the germ killing composition, or reactants providing in situ production thereof, to a germ carrier including substrates of various kinds as well as an enclosed air space.

14 Claims, No Drawings

GERM-KILLING COMPOSITION AND METHOD

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates in general to germ-killing compositions, methods of preparing and using same, and in particular to such compositions advantageously adapted for use in a wide variety of cleaning, sanitizing and disinfecting applications.

2. Description of the Prior Art

The use of chlorine compounds in various types of cleaning, sanitizing disinfecting, etc., compositions is of course well established. Chlorine compounds suggested for use in this regard include, for example, sodium hypochlorite, used in World War 1 as a wound irrigant, and chlorinated phenols such as m-chlorophenol, these compounds having increased bactericidal activity and reduced toxicity, in some instances, when compared to non-chlorinated phenols. Thus, m-chlorophenol has a phenol coefficient of 7.4 (B. typhosus), 5.8 (S. aureus). Other chlorine compounds found advantageous in some form of germ-killing utility include, without necessary limitation, chlorine gas itself, chlorine dioxide, chloramine T, mercuric chloride, calcium hypochlorite (a standard swimming pool disinfectant), chlorapicrin (an exterminator), chloroform (a fumigant) chloradane (an insecticide) zinc chloride (a preservative) and chloromycetin (an antibiotic).

Chlorine dioxide in particular has been found to be an especially effective germ killer. This compound is quite versatile and has long been used as a bleaching agent such as in the oxidizing of the natural colorant present in cotton, wood pulp and other cellulosic fibrous material. Thus, the chlorine dioxide, though performing an oxidizing function, is nevertheless non-injurious with respect to the fibrous material. Additionally, chlorine dioxide has long been used in the treatment of water supplies and is currently available commercially in powder form for use in swimming pools and in liquid form for household and industrial cleaning and disinfecting. In general, chlorine dioxide is superior to gaseous chlorine in the removal of odors, tastes and in destroying and removing algae or other organic material. Moreover, chlorine dioxide is considered at least as effective if not superior to chlorine gas as a bactericide, viruside or sporicide. Chlorine dioxide is further advantageous in that its antiseptic properties are not as sensitive to [PH] *pH* as chlorine, i.e., chlorine dioxide retains its germ killing capacity to a significantly greater extent and over a wider [PH] *pH* range than does gaseous chlorine.

Despite the manifold advantages obtainable with the use of chlorine dioxide for the aforedescribed and related purposes, certain difficulties are nevertheless encountered in practice. Thus, chlorine dioxide as a concentrated gas is explosive and poisonous and accordingly is usually not shipped in the gaseous state to the medium or small user. It has thus become common practice to employ a chlorine dioxide-liberating compound such as sodium chlorite powder which is much safer from the standpoints of storage, shipping and handling. Generation of the chlorine dioxide from the parent sodium chlorite is usually effected in one of three ways as represented as follows:

(1) addition of acid $$[H^+ + NaClO_2 \rightarrow HClO_2 + Na^+; 5HClO_2 \rightarrow 4ClO_2 + HCl + 2H_2O]$$
$$H^+ + NaClO_2 \rightarrow HClO_2 + Na^+ 5HClO_2 \rightarrow 4ClO_2 + HCl + 2H_2O$$

(2) addition of bleach (hypochlorite)

$$2NaClO_2 + NaClO + H_2O \rightarrow 2ClO_2 + 2NaOH + NaCl$$

(3) addition of chlorine $$2NaClO_2 + Cl_2 \rightarrow 2ClO_2 + 2NaCl$$

The generation of chlorine dioxide, hereinafter designated also as $ClO_2$, according to reaction (1) is generally effected with the use of relatively inexpensive inorganic acid, [eg;] *e.g.* hydrochloric acid, sulfuric acid, and the like. For home use, the use of phosphoric or acetic acid (vinegar) is sometimes indicated since they are comparatively safe to handle and generally readily available.

Acid-induced generation of $ClO_2$ from sodium chlorite as heretofore recommended and practiced has proved ineffective for the most part. Thus, it is often found that the acid material utilized tends to react with the $ClO_2$ evolved thereby reducing the effective amount of active ingredients available for useful purposes. In addition, the composition resulting from acidification of the sodium chlorite does not usually exhibit the desired germ-killing efficacy, and particularly from the standpoint of rate of germ kill. To compensate for this deficiency, it becomes necessary to use increased concentration of sodium chlorite and acid which can lead to toxicity problems, [and] particularly when the composition is used in an enclosed air space. Another problem stems from the fact that the composition obtained from the interaction of the sodium chlorite and acid material does not provide a truly effective solvent medium for the active chlorine containing byproducts such as $ClO_2$, chlorous acid and the like. Inhalation of these gaseous components to any significant extent can of course be injurious to health and thus the risk to personal safety becomes an important factor. Significantly, the toxicity problem imposes severe [limitation] *limitations* on the general utility of the disinfectant composition, [and] particularly with respect to treatment of human beings.

SUMMARY OF THE INVENTION

Thus, a primary object of the invention is to provide improved cleaning, sanitizing and disinfecting compositions wherein the foregoing disadvantages are eliminated or at least mitigated to a substantial extent.

Another object of the invention is to provide such compositions having highly effective germ-killing properties with respect to diverse types of germs, germ-producing organisms etc., over a wide range of conditions.

Yet another object of the invention is to provide such compositions wherein loss of active ingredients through fugitive side reaction is minimized.

Still another object of the invention is to provide such compositions having negligible toxicity under the conditions normally prescribed for use and thus highly useful in connection with the germicidal treatment of food receptacles, and utensils, medical hardware, various types of wounds to the human anatomy and the like.

A futher object of the invention is to provide such compositions particularly advantageously adapted for use in ultrasonic cleaning apparatus.

Yet a further object of the invention is to provide such compositions having good stability over a relatively wide [PH] *pH* range.

Still a further object of the invention is to provide methods for disinfecting and sanitizing utilizing such compositions including application of either the germ killing composition or reactants enabling in situ generation thereof to a germ carrier including substrates of various kinds as well as an enclosed air space.

Other objects and advantages of the invention will become more apparent hereinafter as the description proceeds.

DETAILED DESCRIPTION OF THE INVENTION

The foregoing and related objects are attained in accordance with the present invention which in its broader aspects provides a process for the production of a composition having germicidal properties which comprises contacting sodium chlorite with a substantially water soluble acid material selected from the group consisting of organic acids and mixtures thereof with inorganic acid, said acid material comprising at least about 15% by weight of lactic acid and wherein said contacting is carried out in aqueous media and in the presence of sufficient of said acid to lower the [PH] *pH* of the aqueous media to less than about 7.

In further embodiments, the invention provides a process of cleaning, sanitizing and disinfecting utilizing the aforedescribed composition including the application of either the germ killing composition per se, or reactants enabling the in situ production thereof, to a germ carrier including substrates of various kinds as well as an enclosed air space.

The use of lactic acid in the composition and process provided herein is essential. Thus, it is found that this particular compound functions synergistically in combination with sodium chlorite under the conditions hereinbefore prescribed to provide germ-killing compositions of exceptional efficacy. This result is somewhat surprising since ordinarily it would be expected that the lactic acid, as is the case with somewhat similar acid compounds, would react with the by-product chlorine dioxide thereby reducing the effective amount of lactic acid and chlorine dioxide which would otherwise be available for useful purposes. Also, the lactic acid salt produced in the reaction might ordinarily be considered an impurity in a bleaching operation or when disinfecting and removing organic material from a water supply. However, in the present invention, such undesired side reactions, as well as accompanying deleterious effects are evident, if at all, to only a negligible extent.

In formulating the instant compositions, the lactic acid is contacted with the sodium chlorite in aqueous media, sufficient of the acid being used to reduce the [PH] *pH* of the composition below about 7. The water requirements are supplied ordinarily by the acid and chlorite which are available in varying concentrations in aqueous solution. The relative proportions of chlorite compound and lactic acid are selected so as to [insure] *ensure* a [PH] *pH* in the aqueous medium below about 7. The necessary amount of acid is of course determined in part by the strength of the acid reagent solution as well as the total dilution of the respective acid and chlorite compositions as mixed. However, the necessary quantities can readily be predetermined by standard technique.

The germ killing composition obtained upon contacting, i.e., reacting, the chlorite and lactic acid comprises a mixture containing chlorine dioxide, chlorous acid, lactic acid and sodium lactate. The equilibrium mixture of the foregoing materials appears to be in the form of a complex, analyses indicating the presence of at least the ingredients enumerated. The mixture or complex is relatively stable; however, for optimum germ killing results, the composition should be used within a period of up to about 48 hours following its formation. However, if the lactic acid and chlorite compounds are isolated from each other by separate packaging, which may be accomplished using a unitary or common container, little in the way of limitation exists as regards shelf life provided contacting of the chlorite and lactic acid materials be prohibited until used.

Thus, the chlorite and lactic acid materials may be confined within separate chambers of an aerosol type container provided with valve dispensing means actuatable by the application of slight finger pressure to permit substantially simultaneous mixing and discharge of the chlorite and lactic acid components in the form of a fine spray. The necessary aerosol pressure can be supplied by the use of well known propellant gases including hydrocarbons and/or halogenated, [eg] *e.g.*, chlorinated, fluorinated, hydrocarbons. The amount of propellant gas used should be such as to permit substantially complete expulsion or evacuation of the aerosol container contents. Container constructions useful in this regard are in any event well known in the art.

Alternatively, the chlorite and lactic acid may be separately packaged but sold as a unit bearing proper instructions for mixing and use by the home consumer.

The product composition is advantageous in a number of respects. The outstanding germ-killing properties of the composition as regards, for example, bacteria including without necessary limitation, S. aureus, S. albus, Psuedomonas, E. coli, Proteus vulgaris, Strep pyogenes, Candida albicans (dried) spores, B. subtilus (dried) spores and the like, proved particularly surprising in view of the low temperature of the composition used for the kill (approximately 50° C.) as well as the low toxicity level of the composition. Moreover, complete kill of the microrganisms tested is obtained within a period of about 10 minutes when using 50° C. tap water and in less than 5 minutes when using the composition in an ultrasonic cleaner.

Extensive testing establishes the instant compositions to be even less irritating and toxic than, for example, hypochlorite bleach, the latter having long been established to be relatively non-toxic, topically. In general, solutions of $ClO_2$ are not considered to be hazardous and are discharged as a matter of course by textile processors into streams, rivers, etc without harmful result; in fact, such solutions are commonly used to purify fish tanks in public and home aquariums. In addition, $ClO_2$ is used as a preservative for various foodstuffs including cottage cheese and to sanitize food containers which do not require rinsing after such treatment. The instant compositions are even less toxic than conventional $ClO_2$ germicidal solutions and accordingly can be effectively applied to the aforementioned purposes as well as in the treatment of an open wound, the scrubbing of surgeon's hands, etc. When used as a wound irrigant, the use of buffering agent to insure maintenance of a compatible [PH] *pH* often proves advantageous.

Without intending to be found by any theory, the following is postulated in explanation of the truly outstanding germ-killing properties obtainable with the compositions of the present invention. Thus, $ClO_2$ is about five times as water soluble as chlorine and thus much less likely to be lost through volatilization. Moreover, the chlorite ion is significantly less corrosive than the hypochlorite ion to the extent that, in the bleaching of cloth, for example, the presence of $ClO_2$ serves to protect the cloth from the degradative action of the hypochlorite. The bactericidal power of bleach is generally attributed to its ability to diffuse through cell walls and reach vital parts of the bacteria, the killing action resulting from the reaction of hypochlorous acid with the enzyme, triosephosphate dehydrogenase. Other authority holds that the $ClO_2$ accelerates the metabolism of a bacterial cell to the detriment of cell growth. Yet other credible authority asserts that the chlorine ion in $ClO_2$ goes through as many as 8 possible oxidation states in passing through a spore wall. As an algaecide, $ClO_2$ destroys the chlorophyll, breaks down the cell until water is lost from the protoplasm, and thereafter completely destroys or oxidizes the cell so there is no slimy residue on water filters. The presence of the lactic acid appears to enhance or augment the aforedescribed mechanisms. For example, lactic acid, being a natural by-product of muscular exertion, and the frementation of a wide variety of bacteria is not a "foreign" body in a bacteria environment as are other and closely related acids. To this extent, the lactic acid is much more able to penetrate the wall of a bacteria cell without "rejection" and in so doing carry with it the $ClO_2$ and/or chlorous acid molecule. Having penetrated the bacteria cell, it is quite possible that the lactic acid and salts thereof affect the cell's metabolic activity resulting in the formation of intermediate compounds particularly susceptible to the germicidal action of the $ClO_2$ or products derived therefrom. In addition, the formation of other semi-stable chlorine intermediates may be facilitated and these or the $ClO_2$ could inactivate enzymes in critical metabolic processes. Furthermore, it is probable that the oxidizing action of the chlorite ion additionally present on the outside portion of the cell wall is enhanced by the lactic acid which coats the cell wall.

The foregoing explanations notwithstanding, it has in any even been determined in accordance with the invention that the addition of lactic acid in particular to the sodium chlorite material results in a germ-killing composition of outstanding efficacy.

The instant germ killing compositions are particularly effective for use in ultrasonic cleaner devices. The germ-killing properties of ultrasonics alone or cavitation has been studied for years. If intensities are high enough, e.g., over 100 watts per square centimeter, cavitation will not only kill all cells but break them open. However, in an ordinary ultrasonic cleaner, the intensities are far smaller being on the order of 1 watt per square centimeter. However, at this intensity level, the [bacterial] *bacteria* may well culture at a faster rate than if not sonicated due to separation of bacterial dumps and particles. However, the use of the instant germ-killing compositions in ultrasonic cleaning equipment at reduced or ordinary intensity levels proves markedly more effective than germ killing compositions heretobefore provided. Thus, the instant compositions are much less toxic, less polluting, more effective at lower temperatures as well as being non-odorous. The use of the instant compositions in ultrasonic cleaning equipment enables the surgeon, dentist food processor, etc, to both clean and disinfect an instrument or device quickly in a single operation. It appears according to such use that bacteria agglomerates are broken up and separated or bacteria [is] *are* removed from the instrument or device resulting in complete exposure of the bacteria to the solution and thus, its germ killing effects. Microscopic bubbles which often surround or otherwise protect the bacteria are broken up. These bubbles as well as the bubbles produced from cavitation become filled with $ClO_2$. The bubbles, which are very small, often attach to scratches, small cracks and other imperfections in the instrument or device being cleaned enabling thorough disinfecting. In addition, cavitation causes the disinfectant composition to bombard the bacteria cell which [facititates] *facilitates* diffusion of the germ killing composition to the internal portions of the bacteria.

Thus, in accordance with the invention, the combination of the advantages inherent in an ultrasonic cleaner device and the superior germ killing properties of the instant compositions provides exceptional means for cleaning, sanitizing and disinfecting a wide variety of substrates providing a locus for the accumulation of bacteria, virus, spores, and the like.

The use of lactic acid alone in combination with the chlorite material constitutes a particularly preferred embodiment of the invention. However, it is also effective to use the lactic acid in combination with other acids including organic and/or inorganic acids. Suitable organic acids include water soluble or dispersible monocarboxylic poly-carboxylic acids containing from 2 to about 16 carbon atoms including by way of example, acetic, citric, sorbic, fumaric, tannic, acid, etc. Suitable inorganic acids include, for example, sulfuric, hydrochloric, phosphoric acid and the like. When using acid mixtures, it is required that the lactic acid comprise at least about 15% and preferably at least about 45% by weight of the total mixture in order to [insure] *ensure* effective results.

Although the use of sodium chlorite is preferred as the $ClO_2$-liberating material, other water solubilizing cations may be used in place of the sodium including other alkali metals such as potassium and alkaline earth metals, the former, however, being particularly preferred.

The terms "substrate" and "germ carrier" as used herein are intended to cover any type of hard surface or carrier which could provide a locus for the accumulation of germs, virus, spores, bacteria, fungii, i.e., all types of parasitic microorganisms. Obvious examples include surgical and dental instruments, food containers, human tissue, swimming pools, household sinks, garbage containers, bathroom applicances, etc. Cleaning action can be enhanced by the addition of wetting agent, the latter being compatible with and devoid of any tendency to react with $ClO_2$. Particularly effective wetting agents for such use are the fluorocarbon [surtactants] *surfactants* commercially available from Du Pont. The instant compositions in aerosol form can be effectively used to destroy airborne or atmospheric germs such as carried within an enclosed air space. The term "germ carrier" as used herein is intended to cover such atmospheric or gaseous carriers.

In some instances, such as the application of the germ-killing composition to the human tissue as a wound irrigant, it may be advisable to include a buffering agent capable of maintaining a [PH] *pH* level compatible with such tissue. Conventional buffers such as alkali metal bicarbonates may be used in this regard.

The instant compositions may be used in a relatively wide concentration range, the essential requirement being that at least a small but effective germ-killing amount be used. The upper limitation on the amount used is in most cases determined by the point beyond which no further beneficial effect is obtained. The necessary effective amount in a particular instance is also affected by such factors as temperature[,] *and* certain types of spectral radiation which can cause loss of $ClO_2$ from the solution. In general, however, it is found that the use of the chlorite compound in amount ranging from about 100 to 500 ppm in the reactant solution with concentrations on the order of about 2700 to 3300 ppm being preferred, provides effective germ killing results.

The following examples are given for purposes of illustration only and are not to be considered as limiting the invention. All parts and percentages are by weight unless otherwise specified.

EXAMPLE 1

To an aqueous solution of sodium chlorite containing 3,000 ppm sodium chlorite is added sufficient of an aqueous lactic acid solution to reduce the [PH] *pH* of the resultant solution to about three. A portion of the solution thus formed is taken and by analysis found to consist of chlorine dioxide, chlorous acid, lactic acid and sodium lactate. The germ killing effects of the composition were tested, using warm tap water (about 50° C.) against the following:

(a) S. aureus
(b) S. albus
(c) Pseudomonas
(d) E. coli
(e) Proteus vulgaris
(f) Strep Pyogenes
(g) Candida Albicans (dried) Spores
(h) B. Subtilus (dried) Spores Testing in each instance is carried out by impregnating a peni cylinder and surical knot with the bacteria specimen identified until saturated. The test specimens were then immersed in the germicidal composition prepared as described. In each case, complete kill of the microorganism is obtained in a period of about 10 minutes.

EXAMPLE 2

Example 1 is repeated except that testing is carried out in an ultrasonic cleaner device at an intensity of 1 watt per square centimeter and at room temperature. In this case, complete kill of the microorganisms tested is obtained in less than 5 minutes.

The foregoing results are particularly surprising in view of the low temperature prevailing during the testing and the relatively low toxicity levels of the germ-killing composition.

When the foregoing examples are repeated but wholly replacing the lactic acid with respectively (a) phosphoric acid, (b) acetic acid, (c) sorbic acid, (d) fumaric acid, (e) sulfamic acid, (f) succinic acid, (g) boric acid, (h) tannic acid, and (i) citric acid, the results obtained in terms of rate of kill and completeness of kill are markedly inferior when compared to the results obtained with lactic acid. Again, this result is somewhat surprising in view of the close relationship of some of the acids tested to lactic acid.

When examples 1 and 2 are repeated but partly replacing the lactic acid with up to about 80% respectively of phosphoric acid, acetic acid, sorbic acid etc., it is found that effective germ killing compositions are obtained although the improved germ killing effects are not as pronounced as those characterizing the compositions of Examples 1 and 2.

A latitude of modification, substitution and change is intended in the foregoing disclosure, and in some instances some features of the invention will be employed without a corresponding use of other features.

What is claimed is:

1. Process for [the production of a composition having germicidal properties] *disinfecting a substrate* comprising contacting *said substrate with a composition comprising* sodium chlorite with a substantially water soluble acid material selected from the group consisting of organic acids and mixtures thereof with inorganic acid, said acid material comprising at least about 15% by weight of lactic acid, [and] wherein said contacting is carried out in aqueous media and in the presence of sufficient of said acid to lower the [PH] *pH* of said aqueous media to less than about 7.

2. Process according to claim 1 wherein said acid material consists solely of lactic acid.

3. Process according to claim 2 wherein said contacting is carried out in ultrasonic cleaner means.

4. Process for disinfecting and sterilizing which comprises contacting a germ carrier with at least a small but effective germ-killing amount of a germicidal composition obtained by reacting sodium chlorite with a [substantiaelly] *substantially* water soluble acid material selected from the group consisting of organic acid and mixtures thereof with inorganic acid, said acid material comprising at least about 15% by weight of lactic acid and wherein said contacting is carried out in aqueous media and in the presence of sufficient of said acid to lower the [PH] *pH* of said aqueous media to less than about 7.

5. Process according to claim 4 wherein contacting said germ carrier is effected by dispensing said germicidal composition from pressurized, aerosol container means equipped with valve dispensing means.

6. Process according to claim 4 wherein said acid material consists solely of lactic acid.

[7. Germicidal composition obtained in accordance with the process of claim 1.]

[8. Germicidal composition obtained in accordance with the process of claim 2.]

9. Process according to claim 1 wherein said contacting is carried out in ultrasonic cleaner means.

10. Process according to claim 4 wherein contacting said germ carrier is effected by dispensing said germicidal composition from ultrasonic spray producing means.

11. Process for [the production of a composition having germicidal properties] *disinfecting a substrate* comprising contacting *said substrate with a composition comprising* sodium chlorite [with] *and* lactic [and] in an aqueous media and in the presence of sufficient of said lactic acid to lower the [PH] *pH* of said aqueous media to less than about 7.

12. Process for disinfecting and sterilizing which comprises contacting a germ carrier with at least a small but effective germ-killing amount of a germicidal composition obtained by reacting sodium chlorite with lactic acid in an aqueous media and in the presence of sufficient of said lactic acid to lower the [PH] *pH* of said aqueous media to less than about 7.

[13. Germicidal composition obtained in accordance with the process of claim 11.]

*14. A process for disinfecting a substrate comprising contacting said substrate with a composition comprising a water-soluble chlorite with lactic acid in an aqueous media and in the presence of sufficient of said lactic acid to lower the pH of said aqueous media to less than about 7.*

*15. A process for disinfecting a substrate comprising contacting said substrate with a composition comprising a $ClO_2$ liberating material with lactic acid in an aqueous media and in the presence of sufficient of said lactic acid to lower the pH of said aqueous media to less than about 7.*

*16. A process for disinfecting and sterilizing which comprises contacting a germ carrier with at least a small but effective germ-killing amount of a germicidal composition obtained by reacting a water-soluble chlorite with lactic acid in an aqueous media and in the presence of sufficient of said lactic acid to lower the pH of said aqueous media to less than about 7.*

*17. A process for disinfecting and sterilizing which comprises contacting a germ carrier with at least a small but effective germ-killing amount of a germicidal composition obtained by reacting a $ClO_2$-liberating material with lactic acid in an aqueous media and in the presence of sufficient of said lactic acid to lower the pH of said aqueous media to less than about 7.*

* * * * *